United States Patent [19]

Kasahara

[11] Patent Number: 5,070,883
[45] Date of Patent: Dec. 10, 1991

[54] EYE MOVEMENT ANALYZING DEVICE UTILIZING PUPIL CENTER-OF-GRAVITY DATA

[75] Inventor: Tatsuya Kasahara, Amagasaki, Japan

[73] Assignee: Konan Camera Research Institute Inc., Hyogo, Japan

[21] Appl. No.: 450,991

[22] Filed: Dec. 15, 1989

[30] Foreign Application Priority Data

Dec. 16, 1988 [JP] Japan .................. 63-319322

[51] Int. Cl.$^5$ ............................................ A61B 13/00
[52] U.S. Cl. ................................ 128/745; 351/209; 351/211
[58] Field of Search ............................ 128/745; 606/4; 351/209, 210, 211, 221, 226, 237, 205, 206; 250/201.2

[56] References Cited

U.S. PATENT DOCUMENTS

| | | | |
|---|---|---|---|
| 3,542,457 | 11/1970 | Balding | 351/16 |
| 3,598,107 | 8/1971 | Ishikawa | 128/745 |
| 3,663,098 | 5/1972 | Merchant | 351/221 |
| 4,102,564 | 7/1978 | Michael | 351/210 |
| 4,373,787 | 2/1983 | Crane et al. | 351/210 |
| 4,543,476 | 9/1985 | Horikawa | 250/201.8 |
| 4,815,839 | 3/1989 | Waldorf | 351/210 |
| 4,993,828 | 2/1991 | Abe et al. | 351/209 |

FOREIGN PATENT DOCUMENTS 3725817 2/1989 Fed. Rep. of Germany ...... 351/209

Primary Examiner—Stephen C. Pellegrino
Assistant Examiner—Robin R. Longo
Attorney, Agent, or Firm—Koda and Androlia

[57] ABSTRACT

A goggle type eye movement analyzing device which can be mounted on examinee's head incorporating a pair of eyepieces positioned in front of the eyes. Each eyepiece includes a light source, a target, and a TV camera which receives light reflected from the eye to observe eye movement. A video analyzing device is connected to the eyepieces so that it records and analyzes signals from the TV cameras which can automatically focus on the proximate area of the iris of the eye.

4 Claims, 2 Drawing Sheets

EYE MOVEMENT ANALYZING DEVICE UTILIZING PUPIL CENTER-OF-GRAVITY DATA

BACKGROUND OF THE INVENTION

1. Filed of the Invention

The present invention relates to an eye movement analyzing device which observes, records and analyzes eye movement in any direction by focusing on the eye, particularly the iris, which moves following a target.

2. Prior Art

As a conventional eye movement recording method, EOG (electro-oculography) is well known and has been used clinically. According to this method, electrodes are placed on the skin around the eyes, and the inherent potential difference between the cornea and retina is used so that the potential differences produced as a result of eye movement are recorded. It is believed that the potential difference is nearly proportional to the rotating anqle of the eyes.

Another method conventionally used is PENG. This method uses the difference in reflection characteristics of infrared light irradiated on the cornea and sclera to detect eye movement.

There is another device for which the applicant of the present application has previously applied for a patent in Japan under the title "Eye movement Testing Device" (Japanese Serial No. 63-145425). This device uses invisible infrared light inside goggles. The goggles have a head-mount so that they can be placed on the head to create a "darkroom" in front of the examinee's eyes. The device thus designed outputs picture signals of eye movement through an infrared detecting television camera.

Among the prior art devices described above, because the EOG method places electrodes on the skin around the eyes, when electric potential changes on the skin are as frequent as those associated with eye movement, noise is generated and the potential difference between the cornea and retina becomes difficult to detect and thus is unstable. Closing the examinee's eyelids to remove the visual fixation that diminishes nystagmic reaction unfortunately causes the problem of vertical nystagmic reaction.

According to the method using reflected infrared light irradiated on the cornea and sclera, horizontal changes in eye movement can be precisely detected. However, the presence of the eyelids restricts eye movement, and the range of eye movement in the vertical and rotational directions becomes very narrow.

In comparison to these methods, the device of Japanese Serial No. 63-145425 uses goggles with a head-mount together with a darkroom in front of the examinee's eyes, facilitating mountinq and dismounting and enabling placement of a target inside the goggles. Thus, the need for elaborate equipment such as installation of separate targets, etc. is eliminated. Moreover, since the goggles are worn on the head, the examinee has a great deal of freedom of movement. The device directly observes, records, and analyzes eye movement with an infrared detector and offers various advantages over the prior art.

However, this device has problems. Though the movement or adjustment of the eyepiece at the specific position where the television camera is placed in front of the eye enables focusing on the proximate area of the iris, the curvature of the eye hinders simultaneous focusing on the center and peripheral areas of the eye. When the iris moves (together with eye movement), object distances change and it becomes difficult to obtain a constant, clear image of the eye, particularly the image around the iris.

A deep focal depth lens with the camera aperture significantly closed would be unable both the center and peripheral areas of the eye to be focussed on at the same time. However, strong illumination is required in this case which would affect the eyes.

SUMMARY OF THE INVENTION

Accordingly, it is a primary object of the present invention to eliminate the problems encountered in the prior art.

A main object of the present invention is to provide an eye movement analyzing device which can focus the television camera on the moving eye, especially in the proximate area of the iris, observe eye movement and facilitate precise analysis according to the movement of the eye including the pupil and the iris, the iris and the sclera, and the blood vessels on the sclera.

Another object is to provide an analyzing device which minimizes eye discomfort when using infrared lights to illuminate the eyes, and yet another object is to provide an eye movement analyzing device which can be used in a lighted room.

In order to achieve these objects, the present invention utilizes a unique structure for an eye movement analyzing device in the form of goggles which are mounted on an examinee's head. The device includes an eyepiece positioned near one eye or both eyes, and a television camera incorporated in the eyepiece so that the camera receives light reflected by the eye(s) in order to observe eye movement. In addition, a video analyzing device is connected to the TV camera to record and analyze signals from the TV camera. Also, the TV camera is installed so that it can constantly focus on the proximate area of the iris of the moving eye.

In addition, a lens is used whose focus is fixed to the curvature of the eye or a lens that can be adjusted to the curvature of the eye of each individual.

Furthermore, an auto focus system is used which automatically focuses on the proximate area of the iris according to the rotational movement of the eye, and the amount of forward or backward movement or any other type of movement of the eye(s).

The auto focus system outputs center-of-gravity data regarding the pupil to a focus control section via a pupil center-of-gravity detector. The focus control section adjusts the amount of lens focus based upon previously calculated correction data.

In addition, in the present invention invisible infrared light is used to illuminate the eye.

Thus, according to the present invention, the goggles, which incorporate an eyepiece near one eye or both eyes, can be put on the examinee's head so that it can move (or face any directions) along with the examinee's head, giving the examinee a great deal of freedom of movement during the eye examination.

The TV camera is installed in the eyepiece so that it observes eye movement by focusing on the proximate area of the iris and that eye movement data is recorded and analyzed by the video analyzing device.

When the iris moves (in conjunction with eye movement), the proximate area of the iris is focused so that clear images of the eye, in particular, images of the proximate area of the iris including the iris, pupil and parts of the sclera can be obtained. (In the prior art, where focusing is performed at a specific position for instance at the position the examinee looking straight ahead, it was very unlikely that accurate focusing would be obtained.) Thus, the device of this invention naturally suites observation of not only the horizontal and vertical eye movement but also rotational movement.

In addition, with the auto focus system, center-of-gravity data regarding the pupil is output to the focus control section via the pupil center-of-gravity detector, and the amount of extension of the lens is controlled based upon previously calculated correction data so that the lens is constantly focused on the pupil.

With the invisible infrared light used to illuminate the eye, there is no glare discomfort to the examinee, allowing examination in a darkroom.

DETAILED DESCRIPTION OF THE INVENTION

Figure 1:
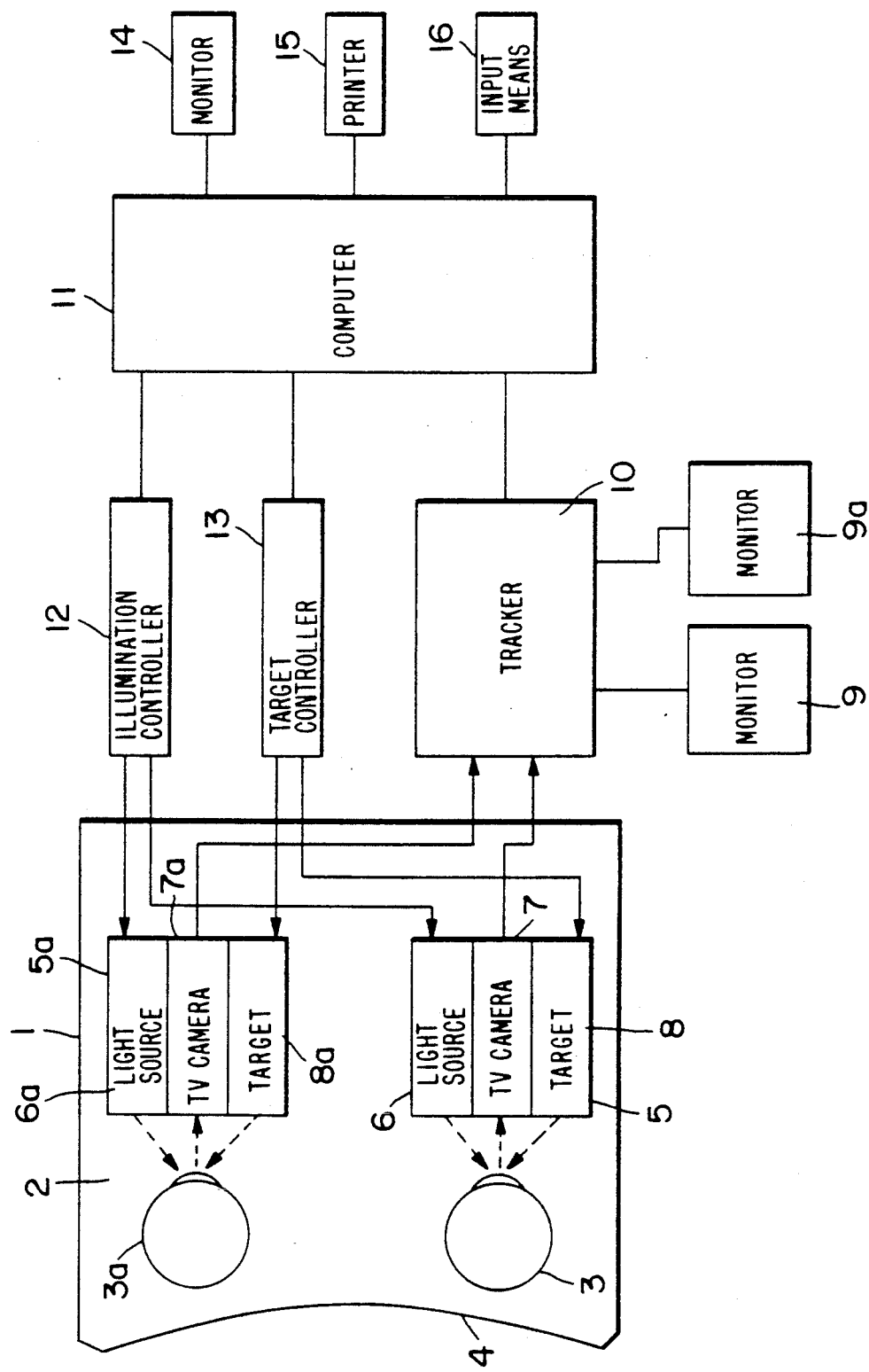
FIG. 1 is a block diagram showing an embodiment of the eye movement analyzing device of the present invention.

Reference numeral 1 designates the goggles which are mounted on the head of an examinee. Reference numeral 2 represents the inside of the goggles 1. The inside 2 of the goggles 1 can be left as a "lighted room" or can create a "darkroom" in the area in front of the eyes by shutting out external visible light. The eyes of the examinee are indicated by numerals 3 and 3a, and the head by numeral 4.

A pair of eyepieces 5 and 5a are provided inside the goggles 1 near the eyes 3 and 3a so that the eyepieces are in front of the eyes. Light sources 6 and 6a which illuminate the eyes are provided in the eyepieces 5 and 5a to form a single unit. Either natural light, visible light or invisible infrared light may be used as the light sources 6 and 6a.

Television cameras 7 and 7a are installed in the eyepieces 5 and 5a. The TV cameras 7 and 7a detect eye movement via the light from the light sources and reflected by the eye so that eye movement is observed, recorded and analyzed via a video analyzing device (described below) which comprises a monitor, computer, etc. The TV cameras 7 and 7a which receive the light reflected by the eye are designed so as to constantly focus on the proximate area of the iris.

The proximate area of the iris referred to here includes one or several of the following elements: the border of the pupil and the iris, the border of the iris and the sclera, and the blood vessels on the sclera. Eye movement is observed and analyzed according to the movement of these element of the eye.

Targets 8 and 8a are provided in the eyepieces 5 and 5a. The targets 8 and 8a are switcheable displays of visible light radiation provided on almost the entire inner surface of bowl-shaped, spherical walls centered on the rotational center of the eyes.

Monitors 9 and 9a are provided so that the optical axes of the TV cameras 7 and 7a are arranged to face the ocular axes of the eyes 3 and 3a via a tracker 10 for detecting the proximate area of the iris. These monitors are controlled by the computer 11.

An illumination controller 12 controls the light sources 6 and 6a via the computer 11, and target controller 13, which controls the targets 8 and 8a, is also controlled by the computer 11.

Reference numeral 14 is a monitor, 15 a printer, and 16 an input device such as a keyboard, mouse, and/or other foot switches which are used via the computer 11 and controls the TV cameras 7 and 7a.

The above-identified elements, that is the monitors 9 and 9a, the tracker 10, the computer 11, the monitor 14, printer 15 and input means 16, make up a video analyzing device which performs observation, recording and analysis of eye movement.

Figure 2:
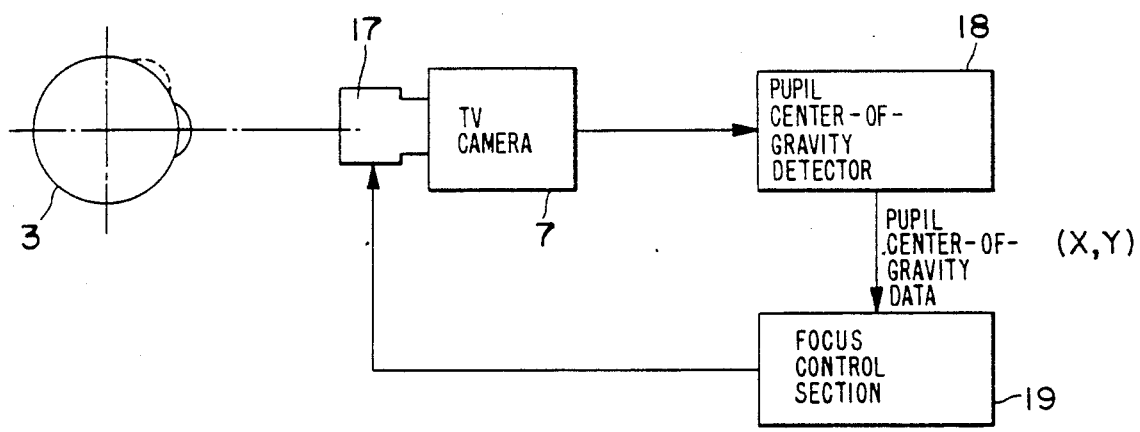
FIG. 2 is a block diagram showing the focus adjustment device for the eye used with the device of FIG. 1.

FIG. 2 illustrates the manner in which focus control is performed by the TV camera. Focus of lens 17 of the TV camera 7 is adjustable by an external drive means (not shown). A pupil center-of-gravity detector 18 (provided in the tracker 10) outputs pupil center-of-gravity data (X, Y) to focus control section 19 (which is also provided in the tracker 10). The focus control section 19 receives the data, adjusts the focus of the lens 17 according to correction data which have been calculated beforehand, and then focuses on the proximate area of the iris.

In the above embodiment, the pupil center-of-gravity data is used as an example of the data used in an auto focus system, but iris center-of-gravity data, iris-pattern center-of-gravity data, or other eye data that can become a reference for focusing may also be used.

A lens that is externally driven and focus-adjustable on curved surfaces may also be used (*Camera Mainichi,* 1980 edition, "Camera Lens White Paper," p. 55).

Figure 3:
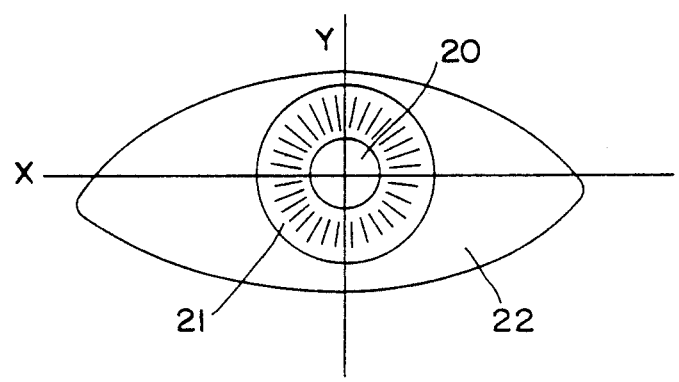
FIG. 3 is a front view of an eye.

In FIG. 3, numeral 20 represents the pupil, 21 the iris, 22 the sclera, X a horizontal axis, and Y a vertical axis of the eye.

The goggles 1 are made of a light alloy or a polyester with glass fiber, which is a light-weight, rigid material. A hollow, rubber air band (not shown) that can be tightened by compressed air to provide free mounting and dismounting on the examinee's head secured on the goggles 1. The inside of the goggles 1 may be designed to form a "darkroom" by using a flexible, light-blocking material such as mortoprene on the inner surface in order to shut out the external visible light.

It would be convenient if the eyepieces 5 and 5a can be moved horizontally, vertically, forward and backward (toward and away from the eyes) so as to match the position of both eyes 3 and 3a and positioned in accordance with the width of both eyes. Though in the device of Japanese Patent Application Serial No. 63-145425 filed by the applicant where the eyepieces are adjusted manually, a transmission mechanism may be used with motors and gears so as to perform automatic drive of the eyepieces instead of manual drive.

As described above, according to the present invention, observation, recording, and analysis of eye movement with a video analyzing device can be performed directly via TV cameras by putting the goggles having eyepieces in front of the eyes, on the examinee's head. Thus, eye movement data is precisely obtained as the targets move without any offensive effects from skin potential or the mounting of electrodes as is found in the prior art. Either one eye or both eyes may be simultaneously observed, and recorded analysis is facilitated by connecting the goggles to a monitor and computer. The examinee, moreover, has a great amount of freedom and a minimum burden when searing the goggles.

The TV camera can focus on the proximity of the iris of the moving eye and can observe eye movement precisely. With connection of the TV camera to a video analyzing device, the image near the iris permits automatic recording and analysis of eye movement, thus greatly enhancing the discovery of lesions and improving treatment of the eyes.

With the use of lenses in the TV camera that can focus on curved surfaces, it is possible to obtain clear eye images.

In addition, by using an auto focusing means that can automatically change the focus position according to the amount of eye rotation (X, Y), a clear image of the proximate area of the iris required for image processing is obtained, and consequent analysis is thus easy and precise.

As a light source for eye illumination, either natural light, visible light, or invisible light are used so long as the video analyzing device can analyze such types of lights.

Furthermore, the proximate area of the iris can be observed when invisible infrared light is employed as an illuminating light source that can select radiation energy so as to not adversely affect the retina or other eye tissue and a wavelength can be selected which is suited for the color of the iris in order to raise image clarity. Thus, an extremely superior eye movement analyzing device is provided by the present invention.

I claim:

1. An eye movement analyzing device, comprising goggles which can be mounted on and dismounted from an examinee's head having incorporated therein an eyepiece provided near one eye or both eyes, a television camera provided on said eyepiece and focused on the approximate area of an iris of the moving eye for receiving light reflected from the eye to observe eye movement, a video analyzing device for recording and analyzing signals from said television camera, wherein said video analyzing device comprises a tracker connected to said eyepieces, and monitor means connected to said tracker for observing light axes of said TV cameras, and a computer system connected to said tracker, said computer system including output and input means, an autofocusing system for said television camera for automatically focusing an approximate area of the iris according to the amount of eye movement, said autofocusing system outputting pupil center-of-gravity data to focus control means via a pupil center-of-gravity detector and said focus control means adjusting extension of said lens based upon previously calculated correction data so that said focus control means focuses on a proximate area of the iris.

2. An eye movement analyzing device according to claim 1, further comprising an infrared video analyzing device employing invisible infrared light which is of a wave length that corresponds to pigments around the iris to illuminate the eye.

3. A device according to claim 1, wherein each of said eyepieces further includes a light source and a target.

4. A device according to claim 1, further including an illumination controller and a target controller connected between said computer system and said light source and target of each of said eyepieces.

* * * * *